(12) United States Patent
Luisi et al.

(10) Patent No.: US 8,721,944 B2
(45) Date of Patent: May 13, 2014

(54) METHOD FOR MARKING A THREE-DIMENSIONAL SURFACE

(75) Inventors: Jerold N. Luisi, Phoenix, AZ (US);
Timothy R. Littlefield, Phoenix, AZ (US); Jeanne K. Pomatto-Hertz, Scottsdale, AZ (US)

(73) Assignee: Cranial Technologies, Inc., Tempe, AZ (US)

( * ) Notice: Subject to any disclaimer, the term of this patent is extended or adjusted under 35 U.S.C. 154(b) by 545 days.

(21) Appl. No.: 12/930,076

(22) Filed: Dec. 27, 2010

(65) Prior Publication Data

US 2012/0161356 A1 Jun. 28, 2012

(51) Int. Cl.
*B29C 59/00* (2006.01)
*A61B 17/00* (2006.01)

(52) U.S. Cl.
USPC .............................. 264/129; 264/162; 602/17

(58) Field of Classification Search
None
See application file for complete search history.

(56) References Cited

U.S. PATENT DOCUMENTS 5,150,525 A * 9/1992 Iai .................................. 33/18.1
2004/0197016 A1* 10/2004 Littlefield et al. ............ 382/128

FOREIGN PATENT DOCUMENTS

WO   WO 2004016438 A1 * 2/2004

* cited by examiner

*Primary Examiner* — Benjamin Schiffman
(74) *Attorney, Agent, or Firm* — Donald J. Lenkszus

(57) ABSTRACT

A method for producing a cranial remodeling device to correct for cranial shape abnormalities is described. One method comprises the steps of: providing cranial remodeling device trim line information; forming device material onto a three-dimensional model of a desired head shape; providing a machine responsive to said trim line information to move a spindle in a plurality of axes over the device material; providing a marking tool carried by the spindle; and operating the machine in response to the trim line information such that the machine moves the marking tool into surface engagement with the device material such that trim lines for the cranial remodeling device are marked onto the device material.

20 Claims, 5 Drawing Sheets

METHOD FOR MARKING A THREE-DIMENSIONAL SURFACE

FIELD OF THE INVENTION

The invention pertains to a method for marking a three-dimensional surfaces, in general, and a method and tool to mark trim lines in the manufacture of cranial remodeling devices, in particular.

BACKGROUND OF THE INVENTION

Cranial remodeling is utilized to correct for deformities in the head shapes of infants. Prior to the development of the Dynamic Orthotic Cranioplasty$^{SM}$ method of cranial remodeling by Cranial Technologies, Inc, the assignee of the present invention, the only viable approach for correction of cranial deformities was surgical correction of the shape of the cranium. Dynamic Orthotic Cranioplasty$^{SM}$ utilizes a treatment protocol in which the DOC BAND® cranial remodeling device is custom produced for each subject to be treated.

In the past, custom cranial remodeling devices were produced by first obtaining a full size and accurate cast of the actual head shape of each subject. This cast was then modified to produce a second or desired head shape model. The second or desired head shape model is used to form the cranial remodeling band for the infant. In the past, the second or desired shaped head shape model was obtained by manually modifying the first cast to form the desired shape model.

Cranial Technologies has maintained a "library" of the casts of the head casts of infant's deformed heads and the corresponding models of the desired corrected head shapes.

Cranial Technologies, Inc. continued its pioneering developments with its proprietary DSI® digital image capturing system and its Digital Surface Imaging®methodology for the time efficient and safe image capture of three-dimensional full head images.

More specifically, the DSI® digital image capturing system was utilized to capture DR® digital data representative of digital images of each cast of a deformed head and each corresponding model of the corrected head shape and store the DSI® digital data for each digital image in first and second databases, respectively. The first and second databases were utilized to train a neural network.

In its continuing efforts, Cranial Technologies further developed a system that utilized these first and second databases to automatically produce digital data representative of a modified head shape from DSI® digital data representative of a deformed head.

The data representative of the deformed head is utilized to provide a full size replica of the modified head shape. On that full size replica, a polymer plastic material is formed as a step in the production of a custom DOC BAND® cranial remodeling device.

After the polymer plastic material is formed on the full size replica, the polymer plastic material must be cut as step in forming a final DOC BAND® cranial remodeling device. The cutting of the material is along trim lines that are customized for the specific customized DOC BAND® cranial remodeling device.

Cranial Technologies further developed a methodology and a computer program implementing that methodology to generate corresponding trim lines for each customized DOC BAND® cranial remodeling device. That methodology is the subject of prior patents owned by Cranial Technologies, Inc.

With the methodology and computer program it is possible for to use a Computer Numerical Control (CNC) machine cutting tool to directly cut the shape of the cranial remodeling device in the polymer plastic material utilizing the computer generated trim line.

Although it is possible to automatically cut along the computer system generated trim lines, we have determined that it is desirable to first draw or mark the trim lines on the polymer plastic surface. Drawing the trim lines allows a product finisher to use skilled judgment to adjust the trim lines as necessary in finishing the product.

We discovered that there is considerable difficulty in drawing or marking the trim lines on the complex three-dimensional surface of a cranial remodeling device. Although CNC machines are particularly useful when cutting a complex three-dimensional bodies, it is difficult to program a tool to just contact the surface of a complex three-dimensional surface with perfect accuracy to provide trim line markings on the surface. The problem is especially aggravated where the surface being marked is a plastic surface. When the plastic surface is digitized, the inherent noise that occurs in the digitization appears as surface variations to the CNC machine We tried to find a marking tool usable in a CNC machine that could be used to draw trim lines as part of our manufacturing process. We found commercially available rigid drawing or marking tools that are suitable for use in CNC machines. However, all of those marking tools require 100% accuracy in locating the surface. If the location of the surface is not perfectly located, the marking tool may impact the surface and break or damage the surface, or the marking tool may not actually touch the surface with the result that the trim line is not drawn, or the marking tool may when drawing the trim line damage the surface in portions, mark the surface in portions, and miss the surface in other portions.

Many commercially available marking tools were investigated for suitability in marking trim lines onto polymer plastic three-dimensional complex surfaces. None of the commercially available marking tools was effective. For these and other reasons, we determined that it was desirable to provide apparatus that would consistently and effectively drawing lines onto the complex surface of a three-dimensional object without risk of damage to the surface and without requiring perfect placement onto the surface.

SUMMARY

In accordance with an embodiment of the invention, a method for producing a cranial remodeling device to correct for cranial shape abnormalities is provided. The method comprises the steps of: providing cranial remodeling device trim line information; forming device material onto a three-dimensional model of a desired head shape; providing a machine responsive to said trim line information to move a spindle in a plurality of axes over the device material; providing a marking tool carried by the spindle; and operating the machine in response to the trim line information such that the machine moves the marking tool into surface engagement with the device material such that trim lines for the cranial remodeling device are marked onto the device material.

The method of one embodiment further includes providing a graphite marking material insert carried by said marking tool to mark the trim lines.

In one embodiment of the invention, a tool for depositing material onto a three-dimensional surface is provided. The tool comprises a first tubular member comprising a first guide surface and a second guide surface. The tool further comprises a second tubular member comprising a first guide surface engaging the first tubular member first surface and comprising a second guide surface engaging the first tubular member second surface. A first resilient member is disposed to urge the second tubular member in a first axial direction relative to the first tubular member. A material holder is disposed axially within the second tubular member. A second resilient member is disposed in the tool to urge the holder in a second axial direction opposite to said first axial direction.

In another embodiment, a tool for marking a three-dimensional surface is provided. The tool comprises a first tubular member adapted to be carried by a motive spindle of a machine of a type capable of moving said spindle along a plurality of axes. A second tubular member is in telescoping engagement with the first tubular member. A first resilient member urges the second tubular member in a first axial direction relative to the first tubular member. A tubular material holder is disposed axially within the second tubular member. A second resilient member urges the holder in a second axial direction opposite to the first axial direction such that the tubular material holder is retained within the tool.

In a further embodiment, apparatus for working a three-dimensional surface is provided. The tool comprises a first tubular member adapted to be carried by a motive spindle of a machine of a type capable of moving said spindle along a plurality of axes. A second tubular member is in telescoping engagement with the first tubular member. A first resilient member urges the second tubular member in a first axial direction relative to the first tubular member. A tool holder is disposed axially within the second tubular member. A second resilient member urges the holder in a second axial direction opposite to the first axial direction such that the tool is retained within the holder.

In another embodiment of the invention, a tool for depositing material onto a three-dimensional surface to mark trim lines for a cranial remodeling device is provided. The tool comprises a first tubular member adapted to be received in a spindle of a 5-axis computerized numeric control mill machine. The first tubular member comprises a first guide surface and a second guide surface. The tool further comprises a second tubular member comprising a first guide surface engaging the first tubular member first surface and comprising a second guide surface engaging the first tubular member second surface. A first resilient member is disposed to urge the second tubular member in a first axial direction relative to the first tubular member. A tubular material holder is disposed axially within the second tubular member. The tubular material holder is adapted to retain marking material therein and extending therefrom. A second resilient member is disposed in the tool to urge the holder in a second axial direction opposite to said first axial direction.

In yet a further embodiment, a tool for marking a three-dimensional surface is provided to mark trim lines onto the surface prior to cutting the surface to form a cranial remodeling device is provided. The tool comprises a first tubular member adapted to be carried by a motive spindle of a machine of a type capable of moving said spindle along a plurality of axes. A second tubular member is in telescoping engagement with the first tubular member. A first resilient member urges the second tubular member in a first axial direction relative to the first tubular member. A tubular material holder is disposed axially within the second tubular member. The tubular material holder is adapted to hold material for marking the surface A second resilient member urges the holder in a second axial direction opposite to the first axial direction such that the tubular material holder is retained within the tool.

In various embodiments of the invention, a graphite marking material is advantageously used in the marking tool to mark trim lines onto a polymer plastic surface

BRIEF DESCRIPTION OF THE DRAWING

The invention will be better understood from a reading of the following detailed description in conjunction with the drawing figures in which like reference designators identify like elements, and in which.

DETAILED DESCRIPTION

U.S. Pat. No. 7,127,101 issued Oct. 24, 2006; U.S. Pat. No. 7,142,701 issued Nov. 28, 2006; U.S. Pat. No. 7,162,075 issued Jan. 9, 2007; U.S. Pat. No. 7,177,461 issued Feb. 13, 2007; U.S. Pat. No. 7,227,979 issued Jun. 5, 2007; U.S. Pat. No. 7,242,798 issued Jul. 10, 2007; 7,245,743 issued Jul. 17, 2007; U.S. Pat. No. 7,280,682 issued Oct. 9, 2007; and U.S. Pat. No. 7,305,369 issued Dec. 4, 2007 are all assigned to Cranial Technologies, Inc., assignee of the present application, and the disclosures contained in each of the patents are expressly incorporated herein by reference.

The aforementioned Cranial Technologies Patents describe systems and methodologies to which the present invention is particularly well suited. In particular, U.S. Pat. No. 7,227,979 describes a methodology and system in which trim lines are generated for customized cranial remodeling devices and in which the trim lines are utilized to produce corresponding customized cranial remodeling devices.

Figure 1:
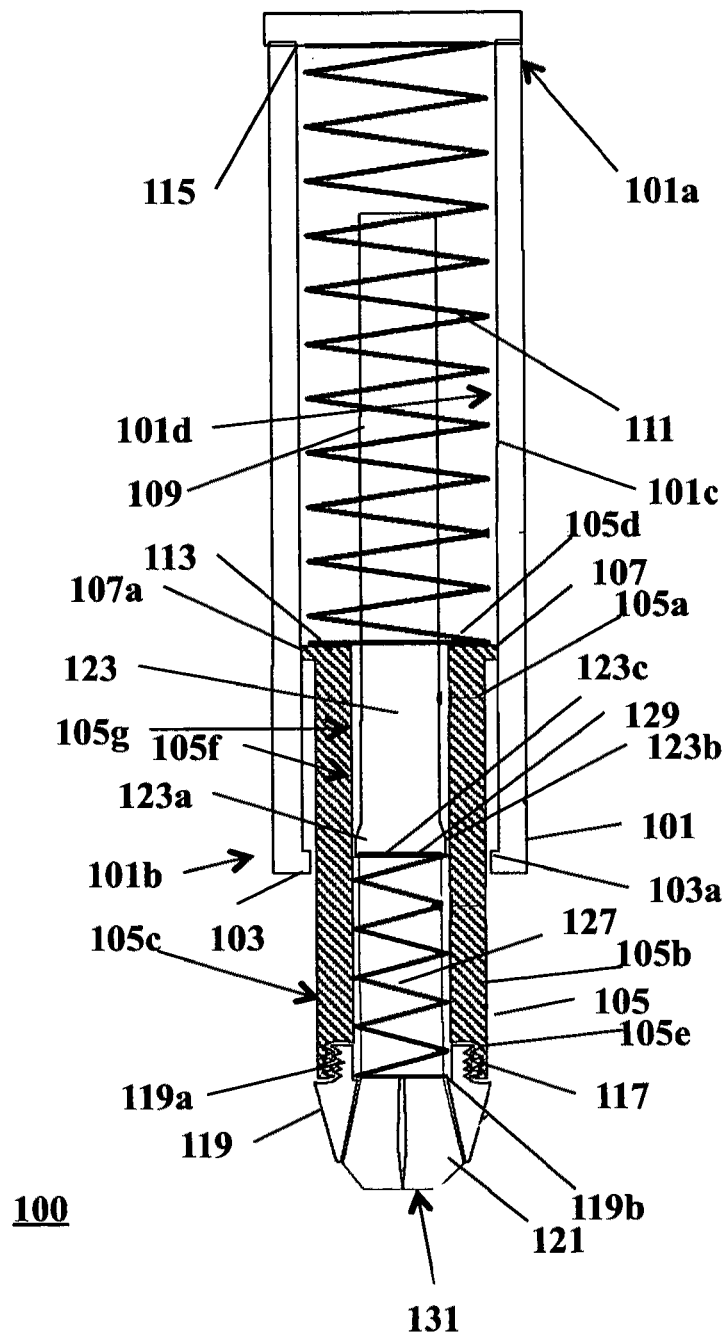
FIG. 1 illustrates an embodiment of the tool of the invention.
Figure 6:
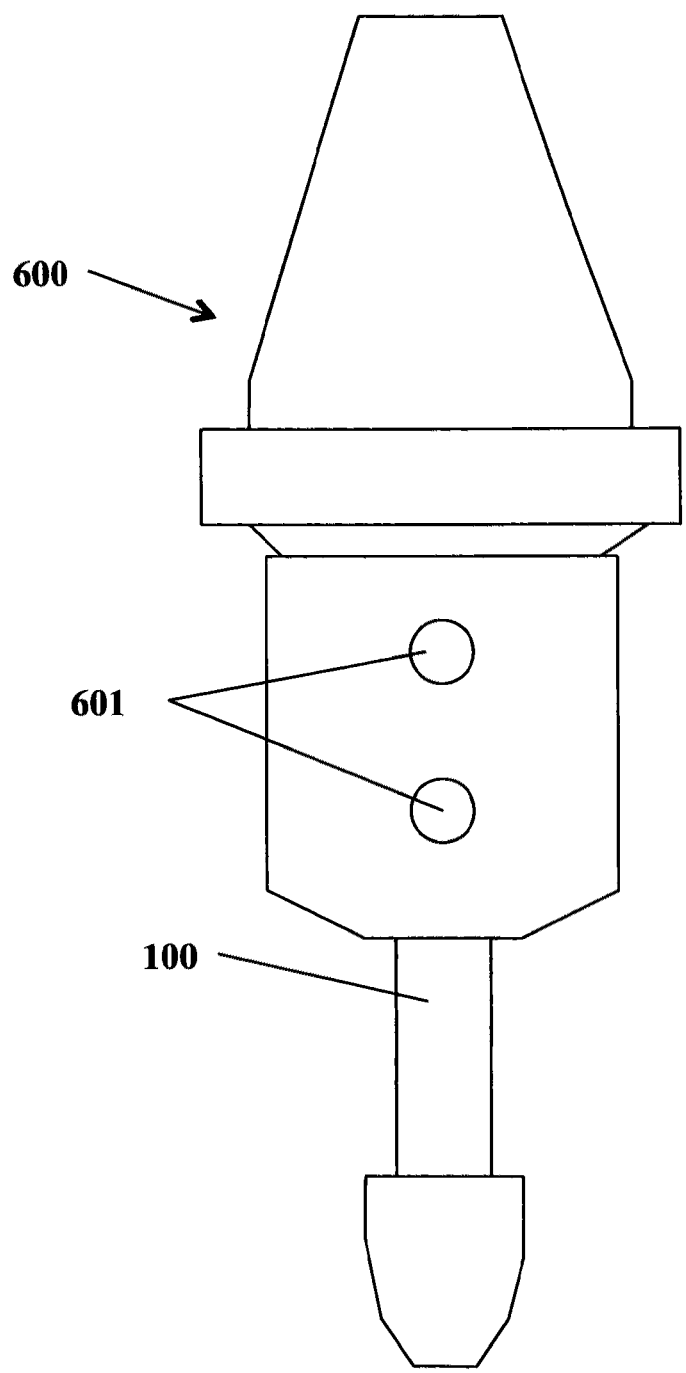
FIG. 6 illustrates the tool of FIG. 1 mounted in a spindle of a machine.

FIG. 1 illustrates one embodiment of a tool 100 in accordance with the principles of the invention. Tool 100 comprises an outer tube 101. Outer tube 101 is of cylindrical shape. In other embodiments, outer tube 101 may be of a different shape. One end 101a of outer tube 101 is closed by a surface 115a. Surface 115a may be provided by an end cap 115 as shown in FIGS. 1-4, or by a surface carried by the machine into which tool 100 is used as shown in FIG. 6.

The other end 101b of outer tube 101 has integrally formed thereon a radially inward extending lip 103 that carries a first guide surface 103a. The inner wall 101c of outer tube 101 provides a second guide surface 101d.

A second or inner tube 105 is disposed partially within and telescopically extending from outer tube 101. The end 105a of inner tube 105 disposed within outer tube 101 has a radially outward extending lip 107. Lip 107 carries a first guide surface 107a. First guide surface 107a slideably engages second guide surface 101d of outer tube 101. The outer wall 105b of inner tube 105 provides a guide surface 105c. Guide surface 105c slideably engages second guide surface 101d of outer tube 101.

A first resilient device or spring 111 is disposed within outer tube 101. One end of spring 111 engages surface 115. The other end of spring 111 engages the top surface 105d of inner tube 105. Spring 111 is selected such that inner tube 105 extends outside of outer tube 101a predetermined distance as shown in FIG. 1.

The other end 105e of inner tube 105 carries a tapered outer collar 119 of a chuck or collet assembly 131. Collar 119 may be affixed to inner tube 105 by any one of a number of conventional means. In the embodiment shown in the drawing figures collar 119 has a threaded portion 119a carrying threads that engage mating threads carried by inner tube 105.

A tubular marking lead or working tool or implement holder 123 is telescopically disposed within inner tube 105. Implement holder 123 includes a collet 121. Implement holder 123 includes a lip 123a that forms a guide surface 123b.

The inner surface 105f of inner tube 105 includes a guide surface 105g. Guide surface 105g is slidingly engaged by guide surface 123b of implement holder 123.

A second resilient member or spring 127 is disposed within inner tube 105. One end of spring 127 engages an annular surface 119b carried on the inside of collar 119. The other end of spring 127 engages a surface 123c of holder 123. Spring 127 is selected such that it urges implement holder 123 into inner tube 105.

Figures 4, 5:
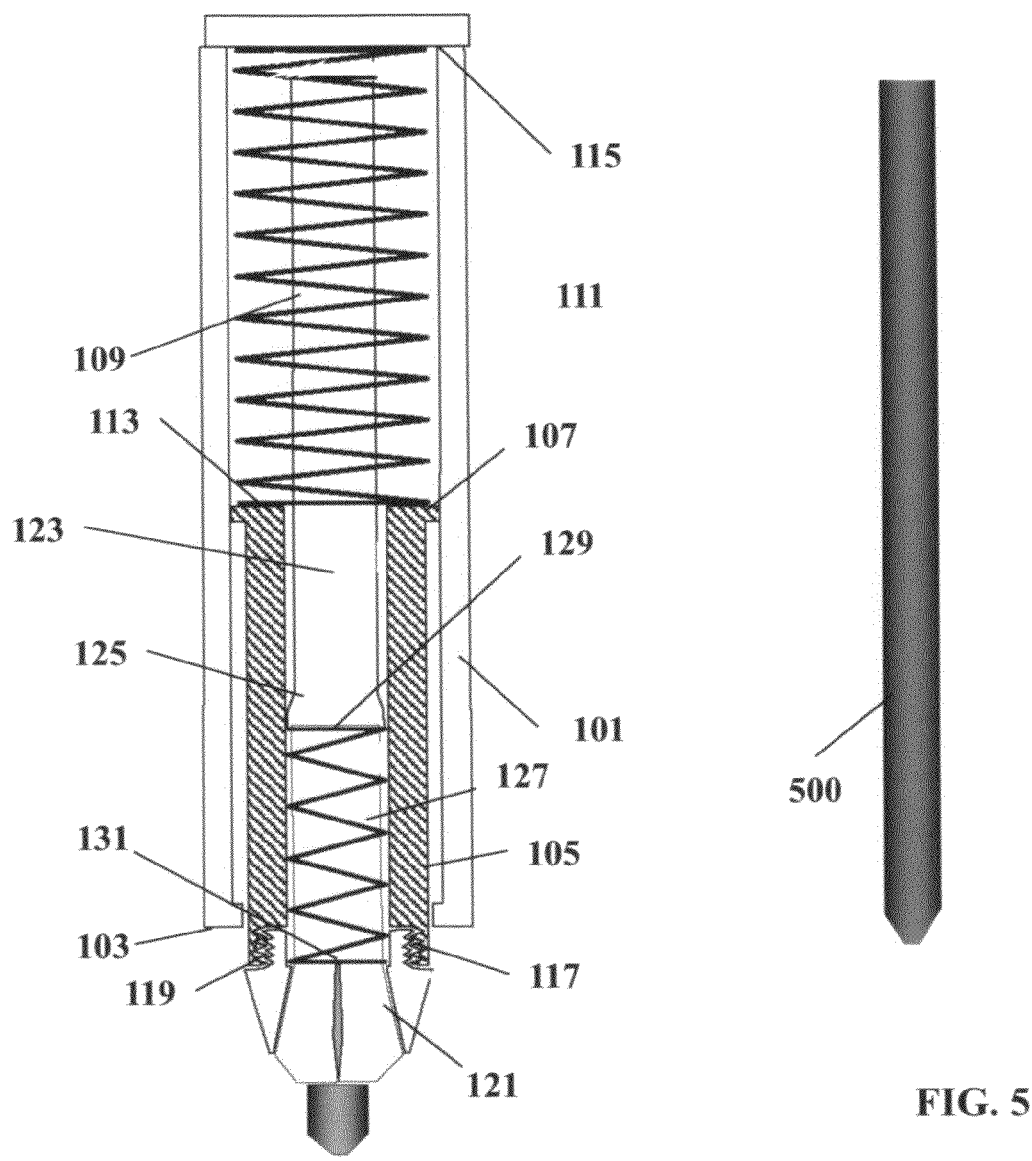
FIG. 4 illustrates the tool of FIG. 1 in a third operational state.
FIG. 5 shows an insert of marking material.

In the embodiment shown, an insert 500 of a marking material such as that shown in FIG. 5 is utilized to mark trim lines. It has been determined that use of graphite marking material is particularly advantageous on the polymer plastic material that is utilized in the Doc Band®.

Figure 2:
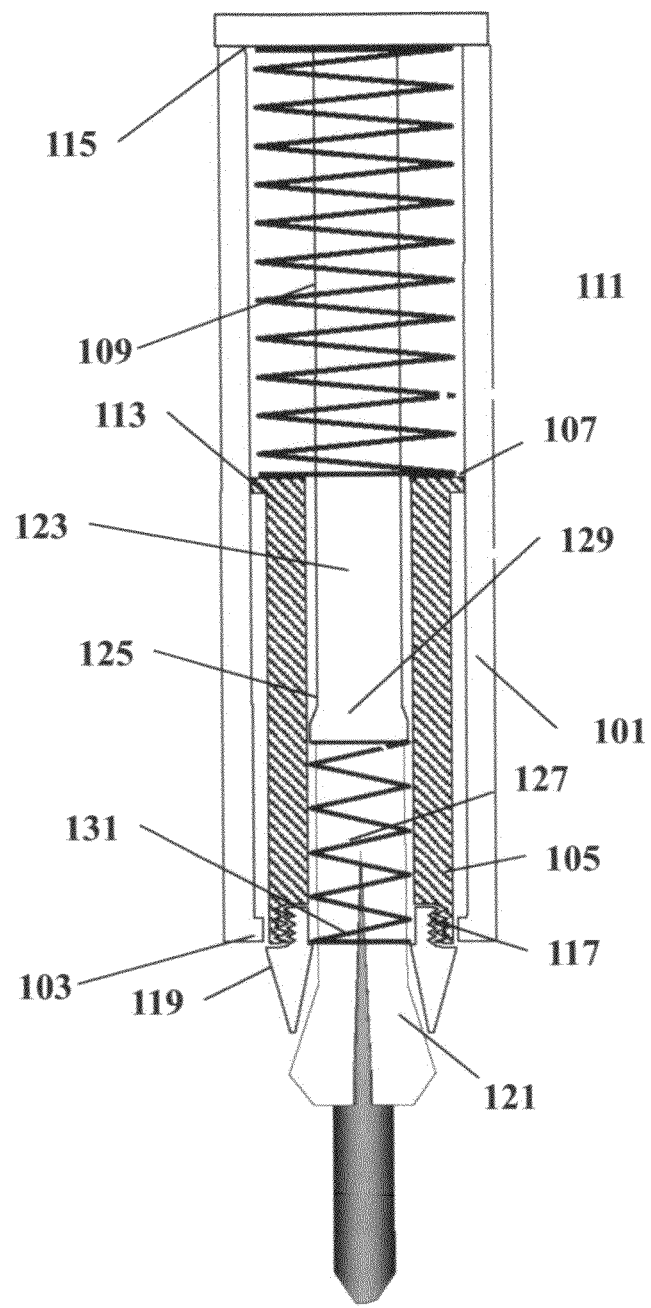
FIG. 2 illustrates the tool of FIG. 1 in a first operational state.

To install insert 500 into tool 100, collar 119 is pushed such that inner tube 105 is fully inserted into outer tube 101. Spring 127 carries the top of holder 123 into engagement with surface 115. As collet 121 disengages collar 119 it spreads or opens such that insert 500 may be installed into holder 123 as shown in FIG. 2.

Releasing collar 119 results in spring 127 urging holder 123 away from collar 119. In this position, collet 121 firmly grips insert 500 and retains it in tool 100. In addition, spring 111 urges inner tube away from surface 115 such that tool 100 and insert 500 are in the position shown in FIG. 3

Figure 3:
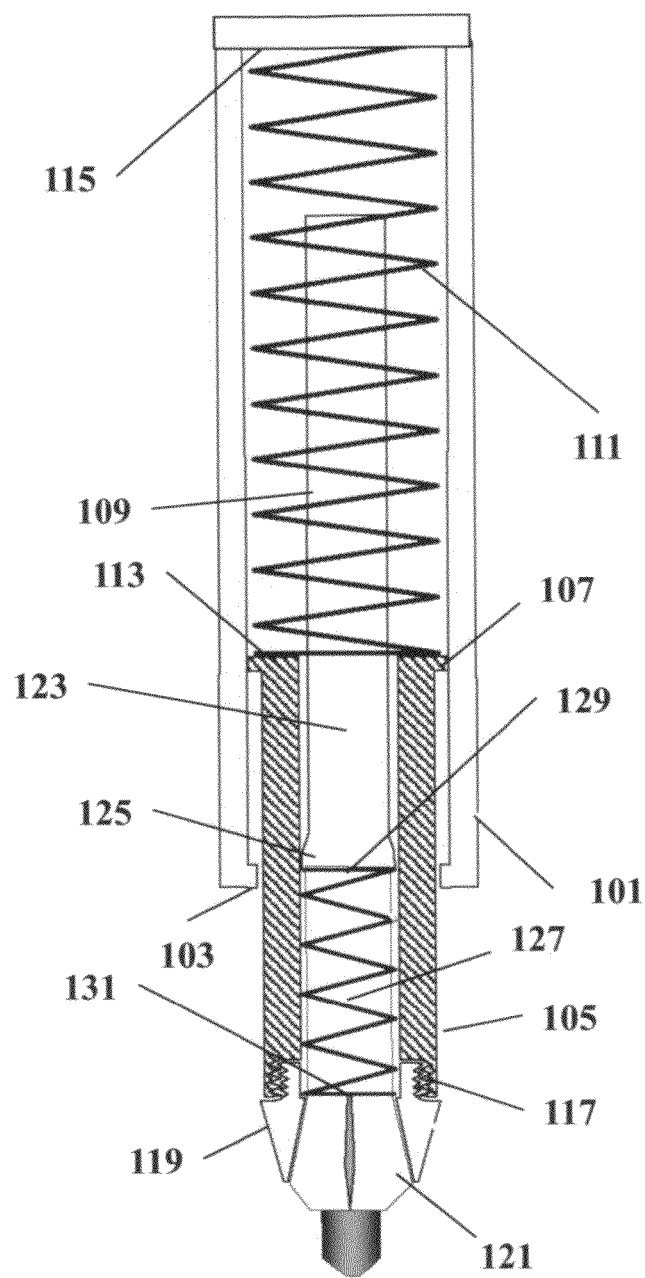
FIG. 3 illustrates the tool of FIG. 1 in a second operational state.

With spring 111, tool 100 may operate in a range of positions from a first position shown in FIG. 3 to a second position as shown in FIG. 4.

Turning now to FIG. 6 tool 100 is inserted into a spindle 600 of a machine that is not shown. Tool 100 is affixed to spindle 600 by setscrews 601. It will be appreciated by those skilled in the art that other approaches may be used to affix tool 100 to the spindle of a machine.

In an embodiment of the invention spindle 600 is that of a commercially available 5-axis computerized numeric control (CNC) machine that can mill a piece stock over three dimensions. The specific machine utilized is a 5-axis commercially available vertical mill that can mill three-dimensional objects with appropriate milling tools.

The assignee of the present invention utilizes the machine to mill a full size model of a desired head shape utilizing computer generated data regarding a desired head shape as described in the patents incorporated herein by reference above. After forming the desired head shape, plastic material is formed onto the head shape. The plastic material must be trimmed by cutting along trim lines to form the desired cranial remodeling device.

The system described in the referenced patents automatically generates trim lines for each custom cranial remodeling device. Tool 100 permits a milling tool in a CNC machine to be replaced with a marking tool that can draw trim lines rather than cut trim lines. The advantage of drawing the trim lines onto the three-dimensional surface rather than cutting trim lines allows for manual adjustments to be made prior to the cutting.

Tool 100 advantageously includes a spring biased mechanism that urges the insert 500 of marking material into engagement with a surface, and when it is in contact with a surface the spring bias permits the insert 500 to rise if the surface "rises" underneath it.

Most printers, plotters and other devices are designed to handle surface in two-dimensions only. Tool 100 can "write" or mark on three-dimensional surfaces. This has the additional advantage of compensating for small deviations or errors in how tool 100 is touched off or "zeroed". Spring loading allows for small errors.

Tool 100 accommodates different surfaces, such as flat, round, elliptical, rough, smooth, etc. Regardless of the surface spring loading makes tool 100 adaptable to the surface terrain.

Although the embodiment describes a marking lead material, other marking materials may be utilized in tool 100. China marker/wax, adhesive/glue, marker, masking material, paint, and fluorescent die are merely representative of the type of material that may be deposited onto a surface utilizing tool 100. The marking can be either permanent or cleanable or erasable depending on the specific application. In one application, wax could be deposited onto a surface to protect the waxed over portion during an etch operation.

By rotating tool 100 at a slow rate while it is in the spindle, the tip of the insert 500 can be kept sharp.

Although the embodiment of tool 100 shown an described above requires that the insert 500 be manually advanced, it will be apparent to those skilled in the art that an automatic self-feed utilizing an additional pressure based resilient mechanism may be utilized.

Although tool 100 has been described with respect to depositing material onto a surface, it should be further apparent to those skilled in the art that a cutting tool bit may also be used in tool 100 in place of insert 500. The use of tool 100 with a cutting tool insert has certain advantages. The spring loading of tool 100 can save a work pieces from being damaged in the event of a programming error that would otherwise result in the cutting tool from smashing into the surface of the work piece resulting in destruction or damage to the work piece and/or the tool.

In another embodiment of the invention, a sensor could be provided in tool 100 to detect a travel limit of inner tube 105 and/or of holder 123. The sensor could provide a signal to the machine to stop operation or cause another response to, for example, stop operation of the machine to avoid tool breakage.

One particular advantage of tool 100 is that it can simplify programming operation of the machine. By way of example, if it is desired to draw a line across a surface that has rises and dips such as a saw tooth, the line could simply be plotted and the spring loading of tool 100 would follow the surface. Otherwise, it would be necessary to program a more complex line with more accelerations/decelerations—a slower, more inefficient process and tougher on the mill.

In accordance with an embodiment of the invention, the above-described tool is utilized in methods for producing a cranial remodeling device to correct for cranial shape abnormalities is provided. One method comprises the steps of: providing cranial remodeling device trim line information; forming device material onto a three-dimensional model of a desired head shape; providing a machine responsive to said trim line information to move a spindle in a plurality of axes over the device material; providing a marking tool carried by the spindle; and operating the machine in response to the trim line information such that the machine moves the marking tool into surface engagement with the device material such that trim lines for the cranial remodeling device are marked onto the device material.

The method further includes providing a graphite marking material insert carried by said marking tool to mark the trim lines.

In the method, the marking tool comprises: a first tubular member adapted to be carried by the spindle; a second tubular member in telescoping engagement with the first tubular member; a first resilient member disposed to urge the second tubular member in a first axial direction relative to the first tubular member; a tubular material holder disposed axially within the second tubular member and the first tubular member; a second resilient member disposed to urge the holder in a second axial direction opposite to the first axial direction such that the tubular material holder is retained within the tool and such that a marking material insert is removably retained by the tubular material holder.

In the embodiment, the material holder comprises a collet adapted to grip said marking material.

The collet comprises a first sloped surface and a collar carried by the second tubular member, the collar having a second sloped surface adapted to releasably engage the first sloped surface. The second resilient member urges the collet first sloped surface into engagement with the second sloped surface to retain the marking material insert in the tool.

In a further embodiment, a method for depositing material onto a three-dimensional surface, comprises: providing material deposit information; providing a machine operable to move a spindle in a plurality of axes over the surface; providing a material carrying tool carried by the spindle; and providing the material deposit information to the machine to move the material carrying tool into surface engagement with the three-dimensional surface such that the material is deposited onto the surface in accordance with the material deposit information.

The method further comprises: providing an insert for the material to be deposited; and carrying the insert by the material carrying tool.

The method further comprises: providing a graphite marking material insert carried by the material carrying tool.

In the embodiment of the method, the material carrying tool comprises: a first tubular member adapted to be carried by the spindle; a second tubular member in telescoping engagement with the first tubular member; a first resilient member disposed to urge the second tubular member in a first axial direction relative to the first tubular member; a tubular material holder disposed axially within the second tubular member and the first tubular member; and a second resilient member disposed to urge the holder in a second axial direction opposite to the first axial direction such that the tubular material holder is retained within the tool.

The method further includes the tubular material holder removably retaining a material insert comprising the material.

The method further includes selecting the material from the group comprising: graphite, marking lead, wax, grease, China marker, marker, masking material, paint, and fluorescent die.

A further embodiment of a method for producing a cranial remodeling device to correct for cranial shape abnormalities, comprises: forming polymer plastic material onto a three-dimensional model of a desired head shape; providing cranial remodeling device trim line information; providing a machine operable in response to the trim line information to move a marking tool in a plurality of axes; providing a marking tool carried by the machine; providing the trim line information to the machine; and utilizing the trim line information to control the machine such that the marking tool marks trim lines on the polymer plastic material in the outline of the shape of a desired cranial remodeling device.

The method of the embodiment further comprises: providing a spindle on the machine; providing a first tubular member adapted to be carried by the spindle, the first tubular member comprising a first guide surface and a second guide surface; providing a second tubular member comprising a first guide surface engaging the first tubular member second guide surface and comprising a second guide surface engaging the first tubular member first guide surface; providing a first resilient member disposed to urge the second tubular member in a first axial direction relative to the first tubular member; providing a material holder carried by the second tubular member; providing a second resilient member disposed to urge the holder into engagement with the second tubular member; and providing an insert held by the material holder; the first tubular member and the second tubular member cooperating with the first resilient member such that the insert marks trim lines onto the polymer plastic material.

The invention has been described in terms of various embodiments. It will be apparent to those skilled in the art that various changes and modifications may be made to the embodiments shown and described without departing from the spirit or scope of the invention. It is intended that the embodiments shown and described are illustrative of the principles of the invention and that the invention not be limited to such embodiments. It is intended that the invention be limited in scope only by the claims appended hereto, with the claims being given the broadest scope permissible under the relevant law.

What is claimed is:

1. A method for producing a cranial remodeling device to correct for cranial shape abnormalities, comprising:

forming device plastic material onto a three-dimensional model of a desired head shape to produce a three-dimensional plastic material;

providing cranial remodeling device digital trim line information for said three-dimensional plastic material;

providing a machine operable to move a spindle in a plurality of axes, said plurality of axes numbering at least five axes, said spindle having a longitudinal axis;

providing a marking tool carried by said spindle;

providing a marking material resiliently carried along said longitudinal axis by said marking tool, said marking material of a type suitable for marking the surface of said plastic material when contacting said surface of said plastic material, said marking tool resiliently carrying said marking material such that said marking material is maintained in continuous contact with said surface of said plastic material to which said marking tool is in close proximity, and said marking material is maintained in resilient contact with said surface when there is relative movement between said marking tool and said surface;

operating said machine in response to said trim line information such that said machine moves said spindle over said surface of said plastic material, said spindle carrying said marking tool proximate said surface of said plastic material and said marking tool carries said marking material into resilient contact with said plastic material such that said marking material contacts said surface of said plastic material to mark continuous trim lines for said cranial remodeling device onto said surface of said plastic material; and subsequent to operating said machine to mark said trim lines, cutting said plastic material to produce said cranial remodeling device.

2. A method in accordance with claim 1, comprising;
rotating said marking material while said marking material contacts said surface of said plastic material.

3. A method in accordance with claim 1, comprising:
providing a graphite marking material insert carried by said marking tool to mark said trim lines.

4. A method in accordance with claim 1, wherein said marking tool comprises:
a first tubular member adapted to be carried by said spindle;
a second tubular member in telescoping engagement with said first tubular member;
a first resilient member disposed to urge said second tubular member in a first axial direction relative to said first tubular member;
a tubular material holder disposed axially within said second tubular member and said first tubular member;
a second resilient member disposed to urge said holder in a second axial direction opposite to said first axial direction such that said tubular material holder is retained within said tool and such that a marking material insert is removably retained by said tubular material holder.

5. A method in accordance with claim 4, wherein:
said material holder comprises a collet adapted to grip said marking material.

6. A method in accordance with claim 5, wherein:
said collet comprises a first sloped surface and a collar carried by said second tubular member, said collar having a second sloped surface adapted to releasably engage said first sloped surface.

7. A method in accordance with claim 6, wherein:
said second resilient member urges said collet first sloped surface into engagement with said second sloped surface to retain said marking material insert in said tool.

8. A method in accordance with claim 7, comprising:
selecting said marking material insert from the group comprising: graphite, marking lead, wax, grease, China marker, marker, masking material, paint, and fluorescent die.

9. A method for depositing material onto a three-dimensional plastic surface, comprising:
providing a machine operable to move a spindle in a plurality of axes, said plurality of axes numbering at least five axes, said spindle having a longitudinal axis;
providing material deposit information;
providing a material carrying tool carried by said spindle, said tool carrying said material, said material being resiliently carried by said tool along said longitudinal axis such that when said tool is carried into proximity to said three-dimensional plastic surface, said material resiliently engages and contacts said three-dimensional plastic surface to deposit said material onto said three-dimensional plastic surface; and
providing said deposit information to said machine;
operating said machine in response to said deposit information to move said spindle over said three-dimensional plastic surface such that said material carrying tool is moved proximate over said three-dimensional plastic surface to carry said material into resilient contact with said three-dimensional plastic surface such that said material is continuously deposited onto said three-dimensional plastic surface in accordance with said material deposit information.

10. A method in accordance with claim 9, comprising;
providing an insert for said material to be deposited; and
utilizing said material carrying tool to carry said insert.

11. A method in accordance with claim 9, comprising:
providing a graphite marking material insert carried by said material carrying tool.

12. A method in accordance with claim 9, wherein said material carrying tool comprises:
a first tubular member adapted to be carried by said spindle;
a second tubular member in telescoping engagement with said first tubular member;
a first resilient member disposed to urge said second tubular member in a first axial direction relative to said first tubular member;
a tubular material holder disposed axially within said second tubular member and said first tubular member; and
a second resilient member disposed to urge said holder in a second axial direction opposite to said first axial direction such that said tubular material holder is retained within said tool.

13. A method in accordance with claim 12, comprising:
removably retaining a material insert comprising said material by said tubular material holder.

14. A method in accordance with claim 13, wherein:
said material holder comprises a collet adapted to grip said material insert.

15. A method in accordance with claim 14, wherein:
said second resilient member acts on said collet to retain said marking material insert in said material holder.

16. A method in accordance with claim 13, comprising:
selecting said material from the group comprising: graphite, marking lead, wax, grease, China marker, marker, masking material, paint, and fluorescent die.

17. A method for producing a cranial remodeling device to correct for cranial shape abnormalities, comprising:
forming polymer plastic material onto a three-dimensional model of a desired head shape;
providing cranial remodeling device trim line information;
providing a spindle;
providing a machine operable to carry and move said spindle in a plurality of axes, said plurality of axes comprising at least five axes, said spindle having a longitudinal axis;
providing a marking tool;
utilizing said spindle to carry said marking tool;
providing said marking tool with marking material;
configuring said marking tool to resiliently carry said marking material along said longitudinal axis;
providing said machine with said trim line information;
operating said machine in response to said trim line information to carry said spindle and said marking tool into proximity to said polymer plastic material such that said marking material resiliently engages the surface of said polymer plastic material;
utilizing said trim line information to control operation of said machine such that said marking tool is moved into proximity to said surface of said polymer plastic material and said marking material resiliently engages said surface of said polymer plastic material; and
operating said machine in response to said trim line information to move said marking tool over said polymer plastic material to deposit said marking material on said surface of said polymer material to mark continuous trim lines on said surface of said polymer plastic material in the outline of the shape of a desired cranial remodeling device;
said resilient engagement of said marking material with said surface of said polymer plastic material is such that variations in said trim line data or in said surface of said polymer plastic material does not interrupt the continuity of said continuous trim lines.

18. A method in accordance with claim 17, comprising:
providing a first tubular member adapted to be carried by said spindle, said first tubular member comprising a first guide surface and a second guide surface;
providing a second tubular member comprising a first guide surface engaging said first tubular member second guide surface and comprising a second guide surface engaging said first tubular member first guide surface;
providing a first resilient member disposed to urge said second tubular member in a first axial direction relative to said first tubular member;
providing a material holder for said marking material carried by said second tubular member; and
providing a second resilient member disposed to urge said holder into engagement with said second tubular member; and
providing a marking material insert held by said material, holder;
said first tubular member and said second tubular member cooperating with said first resilient member such that said marking material insert marks trim lines onto said polymer plastic material.

19. A method in accordance with claim 18, wherein:
said insert comprises graphite material.

20. A method in accordance with claim 18, wherein:
said insert comprises a material selected from the group comprising: graphite, marking lead, wax, grease, China marker, adhesive, glue, marker, masking material, paint, and fluorescent die.

* * * * *